United States Patent
Chen et al.

(10) Patent No.: US 11,882,846 B2
(45) Date of Patent: Jan. 30, 2024

(54) USE OF KEFIR PEPTIDE FOR IMPROVING OR TREATING DEPRESSIVE BEHAVIORS AND RELATED DISEASES

(71) Applicant: National Chung Hsing University, Taichung (TW)

(72) Inventors: Chuan-Mu Chen, Taichung (TW); Hsiao-Ling Chen, Taichung (TW)

(73) Assignee: NATIONAL CHUNG HSING UNIVERSITY, Taichung (TW)

(*) Notice: Subject to any disclaimer, the term of this patent is extended or adjusted under 35 U.S.C. 154(b) by 57 days.

(21) Appl. No.: 17/535,829

(22) Filed: Nov. 26, 2021

(65) Prior Publication Data
US 2022/0346395 A1    Nov. 3, 2022

(30) Foreign Application Priority Data
Apr. 30, 2021   (TW) .................................. 110115819

(51) Int. Cl.
*A23C 9/127*    (2006.01)
*A61P 25/24*    (2006.01)
*A23C 9/13*     (2006.01)

(52) U.S. Cl.
CPC ............ *A23C 9/127* (2013.01); *A23C 9/1307* (2013.01); *A61P 25/24* (2018.01)

(58) Field of Classification Search
CPC ........ A23C 9/127; A23C 9/1307; A61P 25/24
See application file for complete search history.

(56) References Cited

U.S. PATENT DOCUMENTS

2014/0378386 A1* 12/2014 Chen ..................... C07K 2/00
                                                          514/16.9

FOREIGN PATENT DOCUMENTS

TW           201808313 A       3/2018

OTHER PUBLICATIONS

Ebner, "Peptide profiling of bovine kefir reveals 236 unique peptides released from caseins during its production by starter culture or kefir grains", Journal of Proteomics, 2015, 117, pp. 41-57 (Year: 2015).*
Hsiao-Ling Chen, Ying-Wei Lan, Min-Yu Tu, Yu-Tang Tung, Megan Ning-Yu Chan, Hsin-Shan Wu, Chih-Ching Yen, Chuan-Mu Chen; Kefir peptides exhibit antidepressant-like activity in mice through the BDNF/TrkB pathway; J Dairy Sci, Jun. 2021; 104(6):6415-6430, Epub Mar. 23, 2021.

* cited by examiner

*Primary Examiner* — Changqing Li
(74) *Attorney, Agent, or Firm* — MUNCY, GEISSLER, OLDS & LOWE, P.C.

(57) ABSTRACT

The invention discloses that a kefir peptide with an amino acid sequence of SEQ ID No: 2 or a fermentation product comprising the kefir peptide has an antidepressant activity, which means that by administering an effective amount of the kefir peptide or a composition comprising an effective amount of the kefir peptide to an individual with depressive behaviors is capable of effectively improving or alleviating the individual's depressive behaviors. Since the kefir peptide disclosed in the invention is not a chemical compound, the kefir peptide will not have side effects on the human body even taking it on a long-term basis.

6 Claims, 18 Drawing Sheets

Specification includes a Sequence Listing.

Closed arm    Closed arm
Open arm     Open arm

USE OF KEFIR PEPTIDE FOR IMPROVING OR TREATING DEPRESSIVE BEHAVIORS AND RELATED DISEASES

BACKGROUND OF THE INVENTION

Field of Invention

The invention relates to a secondary use of peptide, and more particularly to a use of a kefir peptide for improving or treating depressive behaviors and related diseases.

Related Art

Kefir fermented milk is derived from fermenting milk with kefir grains composed of bacteria and yeast. Many studies have confirmed that kefir fermented milk has efficacies of improving obesity, gastrointestinal diseases, and allergies, and has also efficacies of providing antibacterial activity, improving wound healing, preventing high blood pressure, and anti-oxidation. At present, kefir fermented milk has been further developed into products for the above-mentioned efficacies and sold on the market. However, so far there has been no study confirming that kefir fermented milk is capable of suppressing or improving depressive behaviors.

Depression is a common and serious mental illness, it has become one of the main causes of global morbidity and mortality, and has also become a major public health problem. However, studies have pointed out that due to the complex pathogenesis of depression, clinical treatment is ineffective for about one-third of depression patients, and the conventional antidepressants currently used in clinical practice, such as selective monoamine reuptake inhibitors, tricyclic antidepressants, monoamine oxidase inhibitors, are slower to be metabolized outside the body after being administered to the human body, which means they stay in the body for a longer period of time, which may have a higher risk for depression patients with suicidal tendencies.

Therefore, developing more effective drugs or methods for treating depression without side effects is very important for public health and personal medical treatment.

SUMMARY OF THE INVENTION

A main object of the invention is to provide a use of a kefir peptide for improving or treating depressive behaviors and related diseases, wherein because the kefir peptide disclosed in the invention has an antidepressant activity, the kefir peptide is capable of up-regulating an expression of BDNF (brain-derived neurotrophic factor) in hippocampal tissues and its downstream targets in order to achieve efficacies of effectively suppressing individual depressive behaviors or improving diseases related to depressive behaviors.

Another object of the invention is to provide a use of a kefir peptide for improving or treating depressive behaviors and related diseases, wherein the kefir peptide disclosed in the invention is isolated from a milk fermentation product and is not a synthetic chemical compound, so even if the kefir peptide is taken on a long-term basis, it will not have adverse effects or side effects on the patient's health, which will be beneficial to preventing or treating diseases related to depressive behaviors clinically on a long-term basis.

In order to achieve the above objects, the invention discloses a kefir peptide with an amino acid sequence comprising a sequence as shown in SEQ ID No: 2, and because the kefir peptide has an antidepressant activity and is capable of suppressing or improving depressive behaviors, by administering an effective amount of the kefir peptide or a composition comprising an effective amount of the kefir peptide to an individual suffering from depression or an individual at high risk of depression is capable of regulating an expression of genes or proteins related to depressive behaviors in the individual's hippocampal tissues, such as enhancing an expression of BDNF, enhancing a phosphorylation status of p-Erk1/2 (phosphorylated-ERK1/2) and p-TrkB (phosphorylated-TrkB) in order to improve or suppress the individual's depressive behaviors, thereby achieving efficacies of treating or preventing depressive behaviors or diseases related to depressive behaviors.

Wherein the amino acid sequence of the kefir peptide is as shown in SEQ ID No: 2.

In a disclosed embodiment of the invention, the composition comprising an effective amount of the kefir peptide is a food, a pharmaceutical composition or a functional nutriment.

In one embodiment of the invention, the composition comprising an effective amount of the kefir peptide is a kefir fermentation product, which is obtained by fermenting and reacting cow's milk with kefir grains and then removing the kefir grains.

In one embodiment of the invention, the composition comprising an effective amount of the kefir peptide further comprises a peptide with an amino acid sequence of SEQ ID No: 1.

In one embodiment of the invention, the composition comprising an effective amount of the kefir peptide further comprises a peptide with an amino acid sequence of SEQ ID No: 3.

In another embodiment of the invention, the kefir peptide is used to prepare a BDNF promoter, which means that by administering an effective amount of the kefir peptide to an individual is capable of effectively improving an expression of BDNF in the individual's hippocampal tissues.

DETAILED DESCRIPTION OF THE INVENTION

The invention discloses that a kefir peptide or a fermentation product comprising the kefir peptide has an antidepressant activity, which means that by administering an effective amount of the kefir peptide or a composition comprising an effective amount of the kefir peptide to an individual with depressive behaviors is capable of effectively improving or alleviating the individual's depressive behaviors, and capable of enhancing an expression of BDNF (brain-derived neurotrophic factor) in the individual's hippocampal tissues and a capability of activating the BDNF/TrkB information channel. Therefore, the kefir peptide disclosed in the invention or the composition comprising an effective amount of the kefir peptide is capable of treating or improving depressive behaviors or diseases related to depressive behaviors, and can be developed into related compositions, such as functional foods, nutritional supplements, medicines. In addition, compared with the existing clinical drugs, since the kefir peptide disclosed in the invention is not a chemical compound, the kefir peptide will not have side effects on the human body even taking it on a long-term basis.

Further, when an individual is under pressure or other external factors that cause a reduction in an expression of BDNF in the hippocampal tissues, it will lead to the occurrence of depressive behaviors, and the examples disclosed in the invention prove that by administering the kefir peptide disclosed in the invention or the composition comprising the kefir peptide to an individual is capable of enhancing an expression level of BDNF in the hippocampal tissues and its downstream targets p-TrkB/TrkB, p-Erk1/2/Erk1/2, thereby achieving efficacies of improving the individual's depressive behaviors or diseases related to depressive behaviors.

The "kefir peptide" disclosed in the invention comprises an amino acid sequence of SEQ ID No. 2 or its amino acid sequence is SEQ ID No. 2, and the kefir peptide is prepared by artificial synthesis or a recombinant biological platform, or can be isolated from milk fermentation products.

Figure 1A:
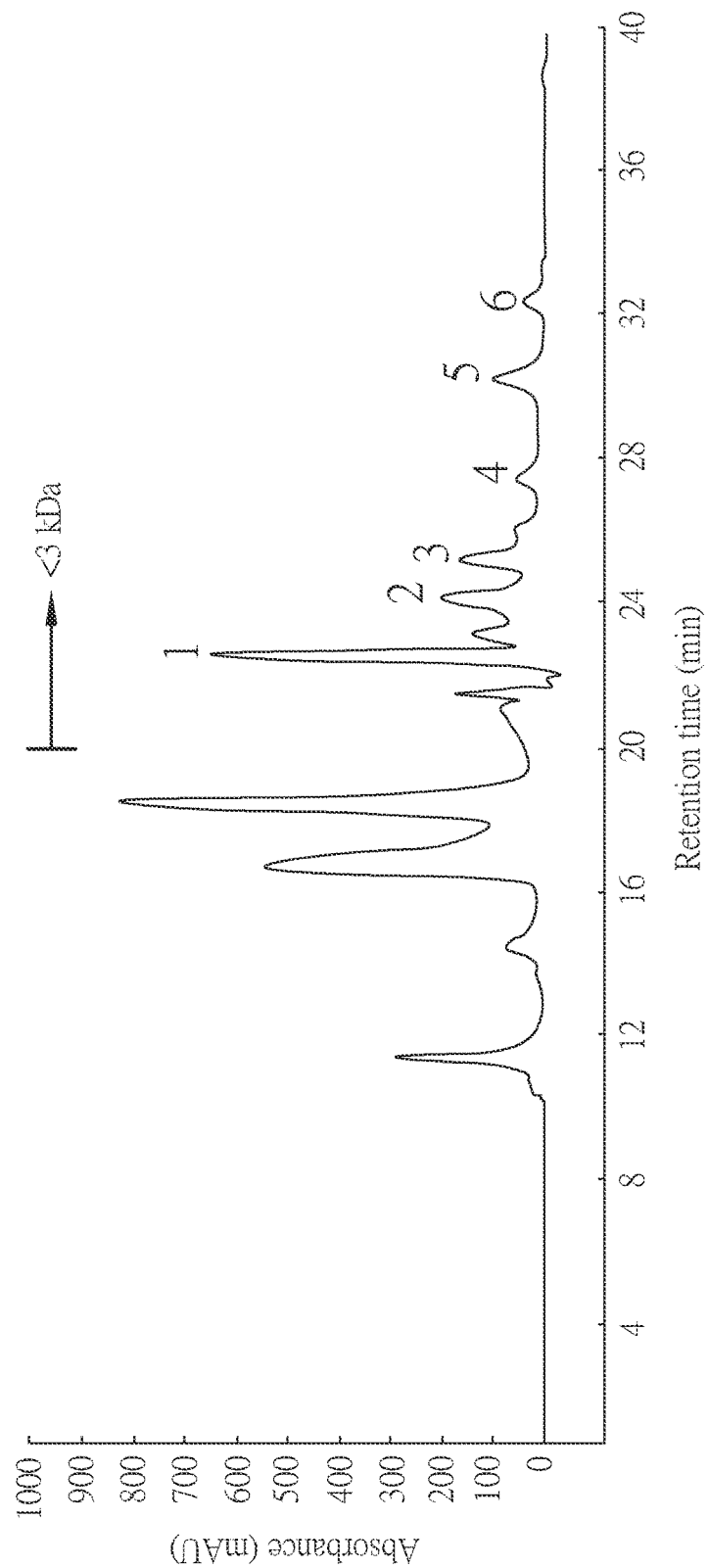
FIG. 1A is a chromatograph obtained after analyzing kefir fermentation product by HPLC.
Figure 1B:
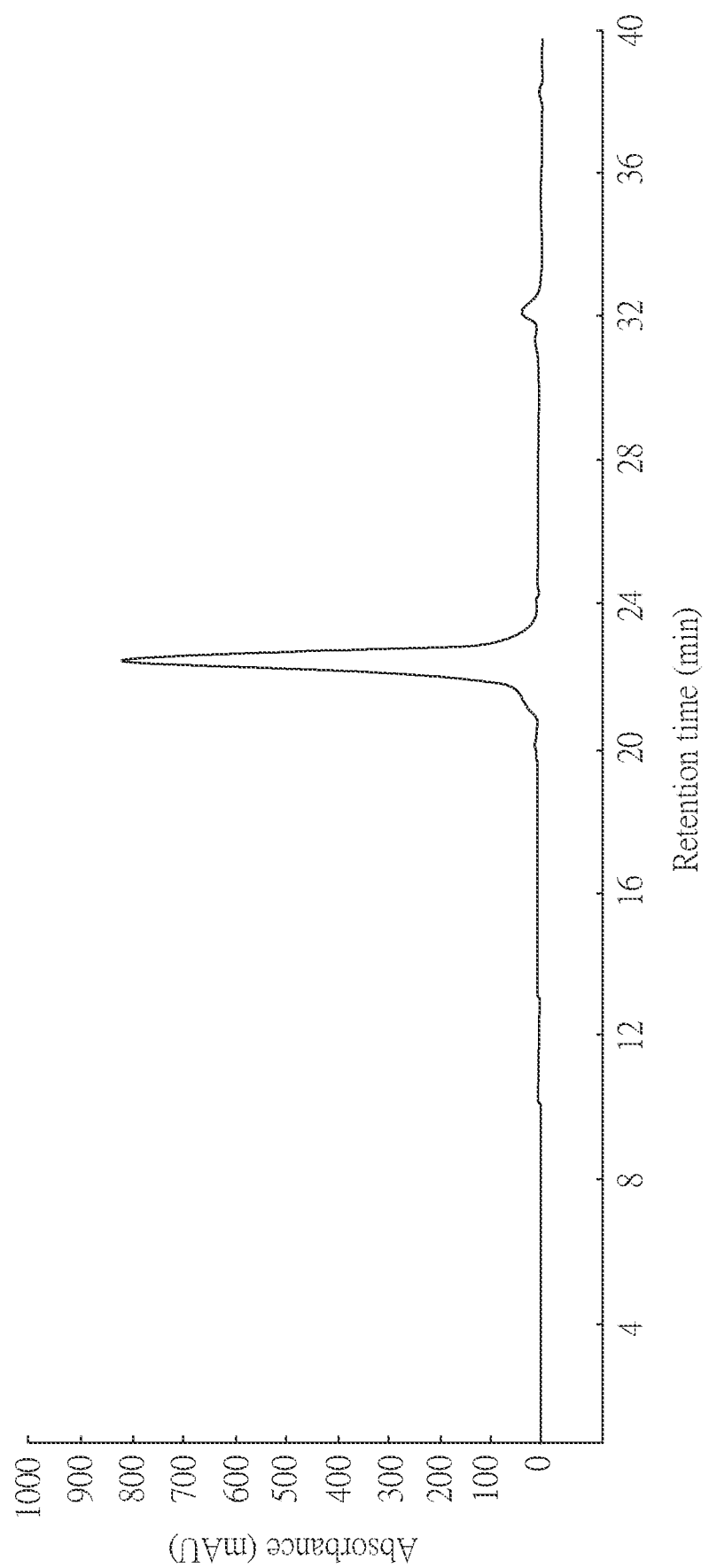
FIG. 1B is a chromatograph obtained after analyzing peptide 1 isolated from kefir fermentation product by HPLC, wherein the retention time of peptide 1 is between 20 and 24 minutes.
Figure 1C:
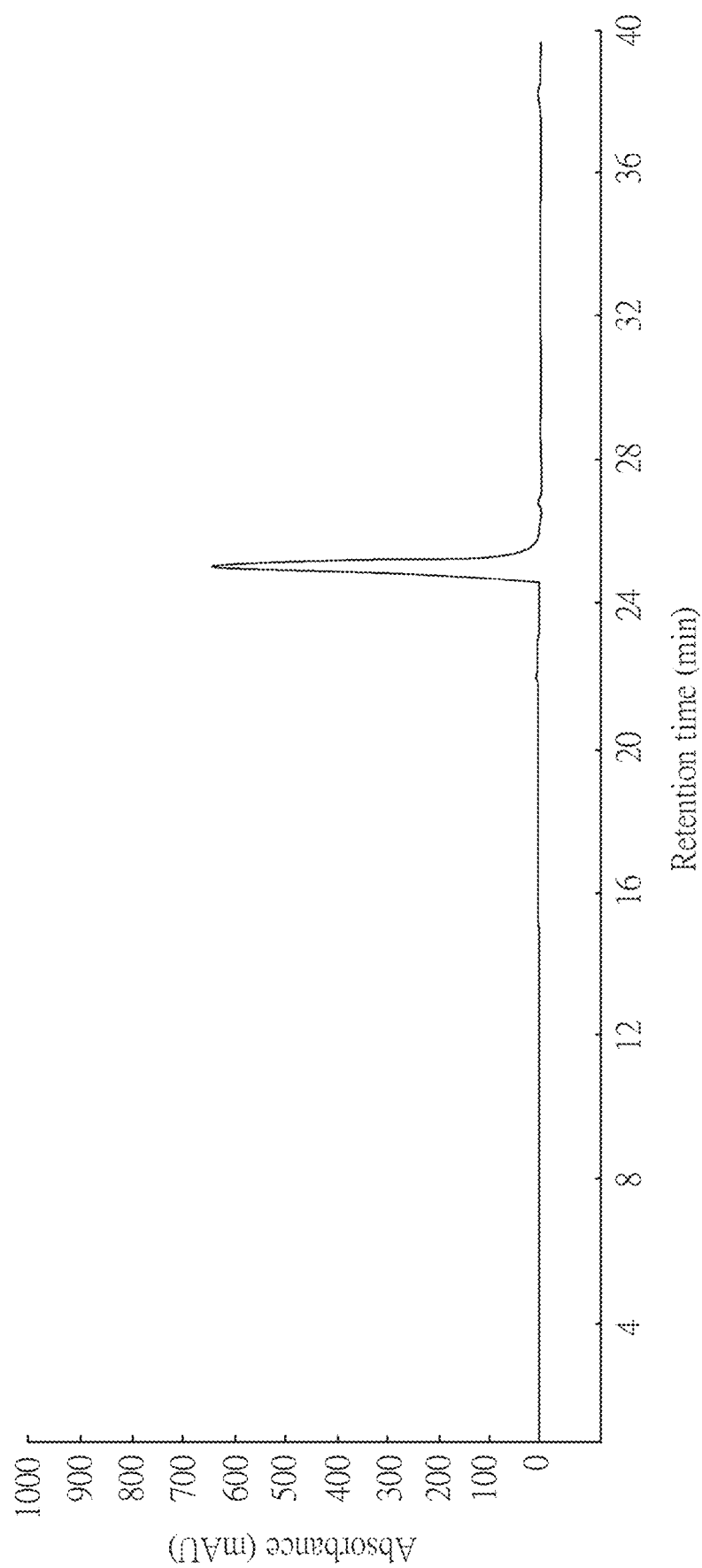
FIG. 1C is a chromatograph obtained after analyzing peptide 2 isolated from kefir fermentation product by HPLC, wherein the retention time of peptide 1 is between 24 and 28 minutes.
Figure 1D:
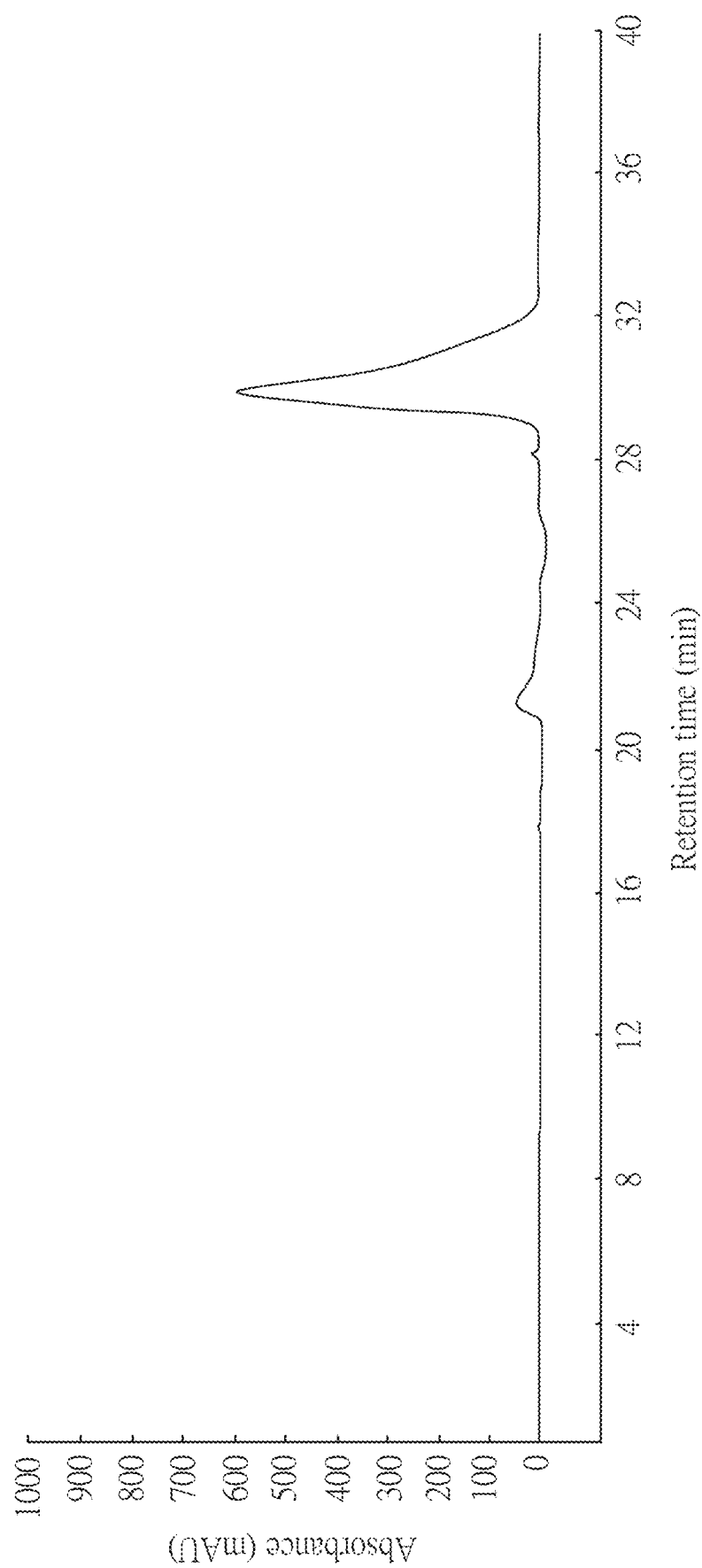
FIG. 1D is a chromatograph obtained after analyzing peptide 3 isolated from kefir fermentation product by HPLC, wherein the retention time of peptide 1 is between 28 and 32 minutes.

For example, the kefir peptide disclosed in the invention can be isolated from a kefir fermentation product, wherein the kefir fermentation product is a mixture obtained by fermenting an animal milk, such as cow's milk with a kefir grain. The kefir fermentation product and the kefir peptide disclosed in the invention are analyzed with HPLC under the following conditions: the detection wavelength is 215 nm, the isolation column is a SEC column, the eluent is 100 mM phosphate buffer solution, 1M sodium chloride and 1 mM ethylenediaminetetraacetic acid (EDTA), pH 6.5, flow rate 0.5 ml/min, the results are shown in FIG. 1A and FIG. 1B, and by comparing the results in FIG. 1A with that in FIG. 1B, it can be known that the kefir fermentation product does comprise the kefir peptide disclosed in the invention.

Hereinafter, in order to verify the technical features and efficacies of the invention, a number of examples in conjunction with figures are illustrated for more detailed description as follows.

CD-1 mice used in the following examples are purchased from the National Laboratory Animal Center (NLAC), Taipei, Taiwan.

The peptide used in the following examples is isolated from kefir fermentation product, and can also be prepared by artificial synthesis.

The data in the following examples are presented in the form of average±standard deviation, and statistical analysis is performed by Duncan's test.

Example 1: Preparation of Peptide

After a milk is fermented and reacted by kefir grains, the kefir grains are removed and the fermented milk is lyophilized to obtain a kefir powder. According to calculations, the peptide content in the kefir powder is calculated as triglycine equivalent, 23.1 g/100 g.

Then, an isolation procedure is performed by HPLC, wherein the conditions used are mobile phase: 100 mM KH2PO4, 1 M NaCl, 1 mM EDTA (pH=6.5), flow rate 0.5 ml/min, detection at 215 nm; a molecular weight of the peptide is analyzed by LC-MS-MC, and the isolated peptide is confirmed and identified by using a library of known peptide sequences. The results are shown in FIG. 1A to FIG. 1D, and the amino acid sequences are shown in Table 1 below.

TABLE 1

The peptides and their sequences

| Serial number in FIG. 1 | Name | Amino acid sequence | Amino acid sequence number |
|---|---|---|---|
| 1 | Peptide 1 | TEIPAINTIASAEPTVH | SEQ ID No: 1 |
| 3 | Peptide 2 | YQEPVLGPVRGPFPI | SEQ ID No: 2 |
| 5 | Peptide 3 | KLHLPLPLVQSWM | SEQ ID No: 3 |

In addition, the peptide 1, the peptide 2 or the peptide 3 can also be synthesized by chemical synthesis.

Example 2: Animal Test

Take 5-week-old CD-1 mice, provide standard laboratory animal feed (Altromin, Germany) and distilled water (dH2O), and keep them for 12 hours at 22-24° C. for light/dark cycles. Before starting the test, each group of mice are raised in an experimental animal room for 1 week to adapt to the environment, and then the mice are randomly divided into 4 groups, and the mice in each of the groups are treated and raised for 8 days (referred to as the first day of rearing to the eighth day of rearing) according to the following conditions:
the first group: take distilled water orally;
the second group: take 150 mg/kg milk powder orally;
the third group: take 150 mg/kg kefir fermentation product orally; and
the fourth group: take 10 mg/kg drug trazodone hydrochloride orally.

After the test, the mice in each of the groups are anesthetized and their hippocampal tissues are isolated, and frozen and preserved for use in subsequent examples.

Example 2: Elevated Plus Maze Test (EPMT)

The mice in each of the groups of Example 1 are treated for 6 hours according to the above conditions on the 7th day of rearing, and then an elevated plus maze test is performed, and paths of the mice in each of the groups within 5 minutes are observed with a camera. The results are shown in FIGS. 2A to 2D, and the time of the mice in each of the groups spent on open arms or closed arms in the elevated plus maze is analyzed, and the results are shown in FIG. 2E to FIG. 2H.

Figure 2A:
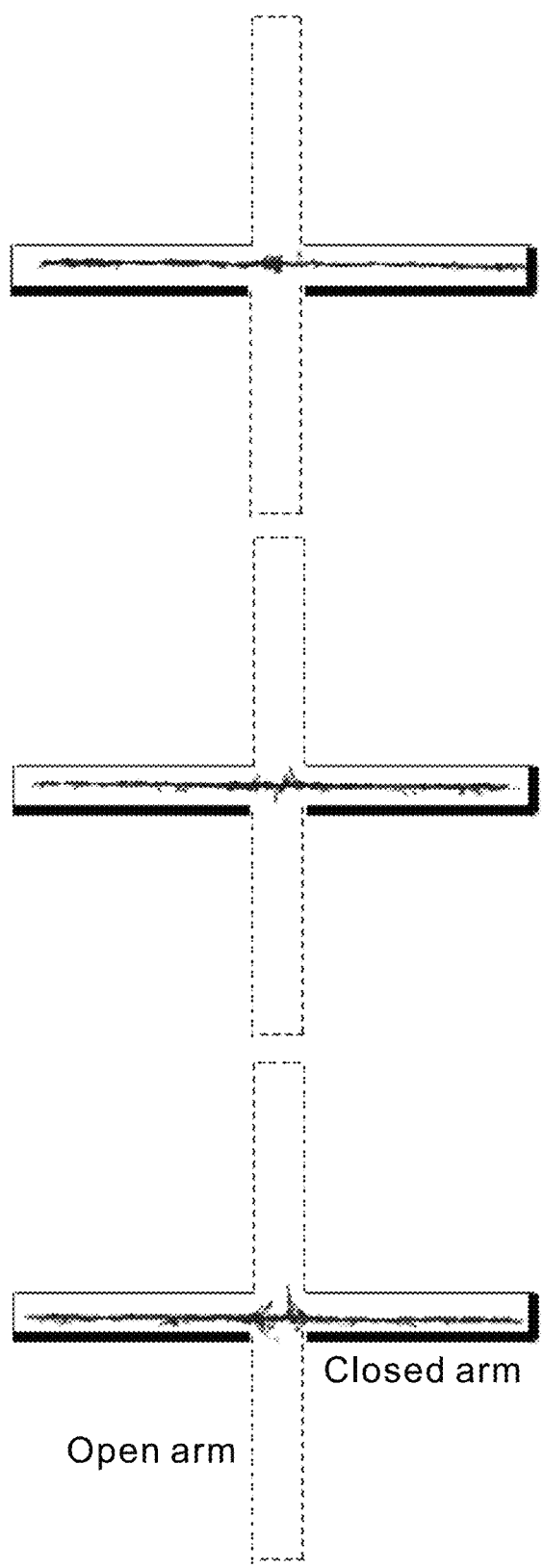
FIG. 2A shows paths of a first group of mice observed by camera in an elevated plus maze test.
Figure 2B:
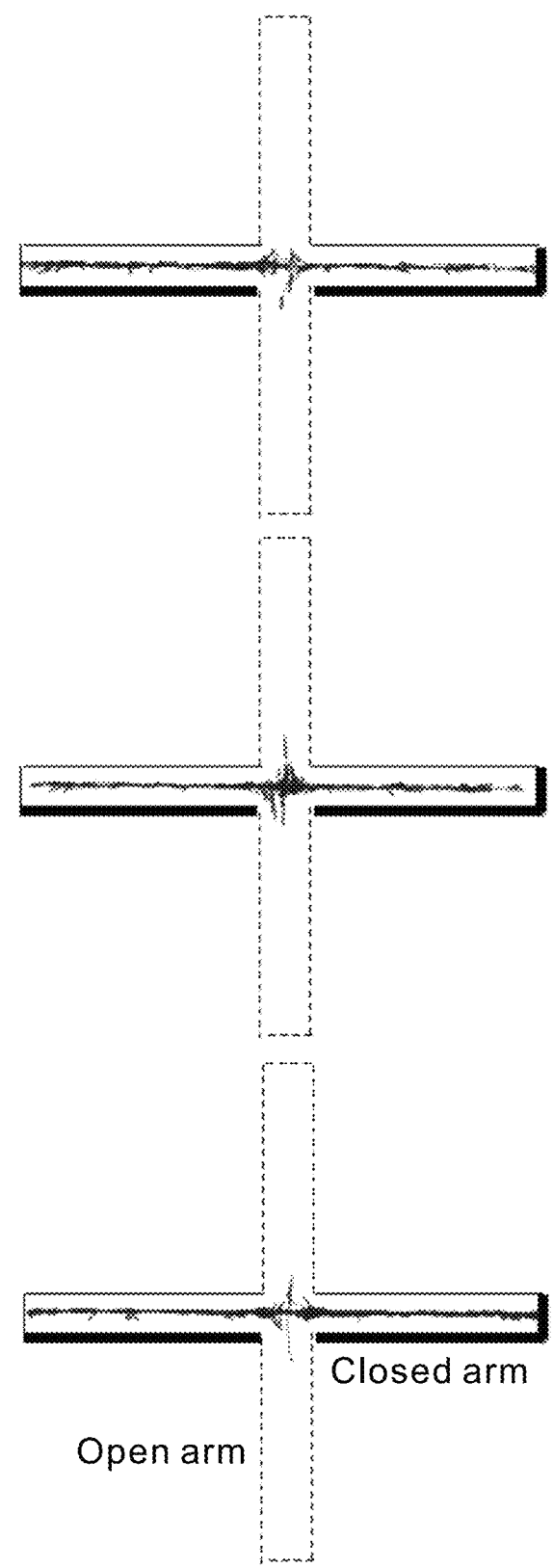
FIG. 2B shows paths of a second group of mice observed by camera in an elevated plus maze test.
Figure 2C:
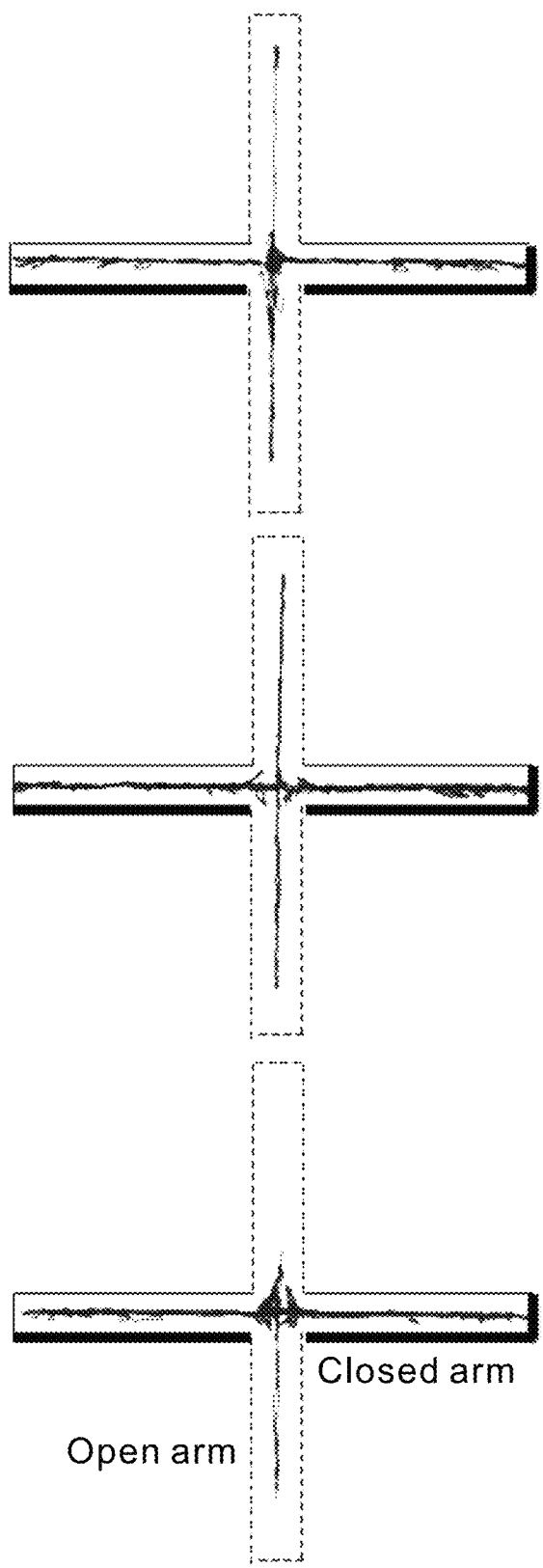
FIG. 2C shows paths of a third group of mice observed by camera in an elevated plus maze test.
Figure 2D:
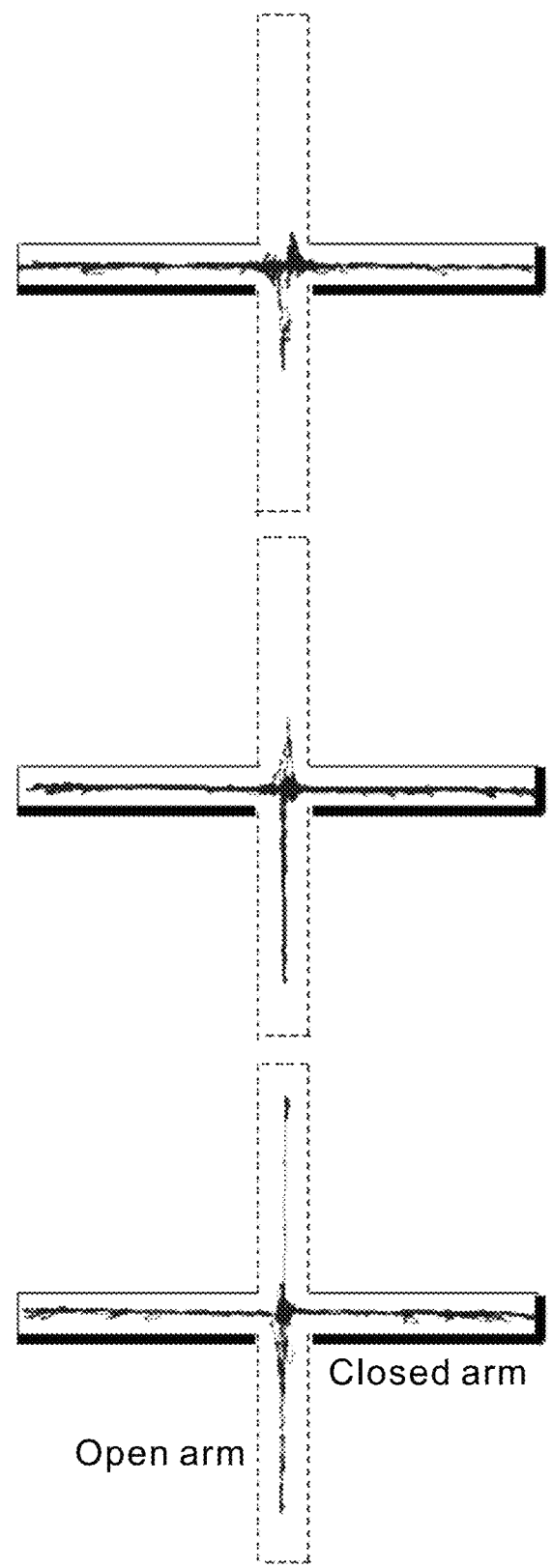
FIG. 2D shows paths of a fourth group of mice observed by camera in an elevated plus maze test.
Figure 2E:
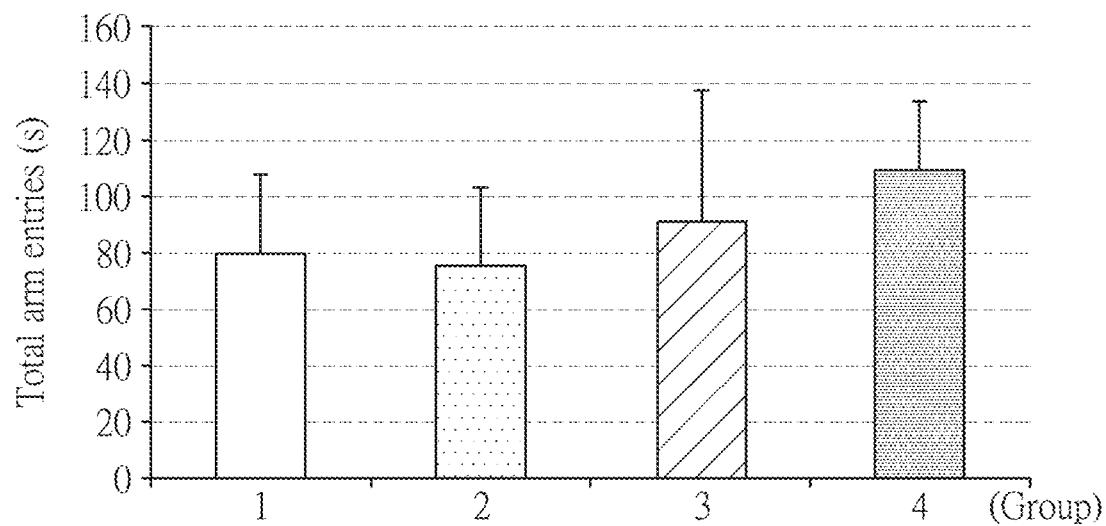
FIG. 2E is the results of statistical analysis of the time it takes for the mice in each of the groups to enter all arm entrances of the elevated plus maze, wherein the "s" of Y axis represents second.
Figure 2F:
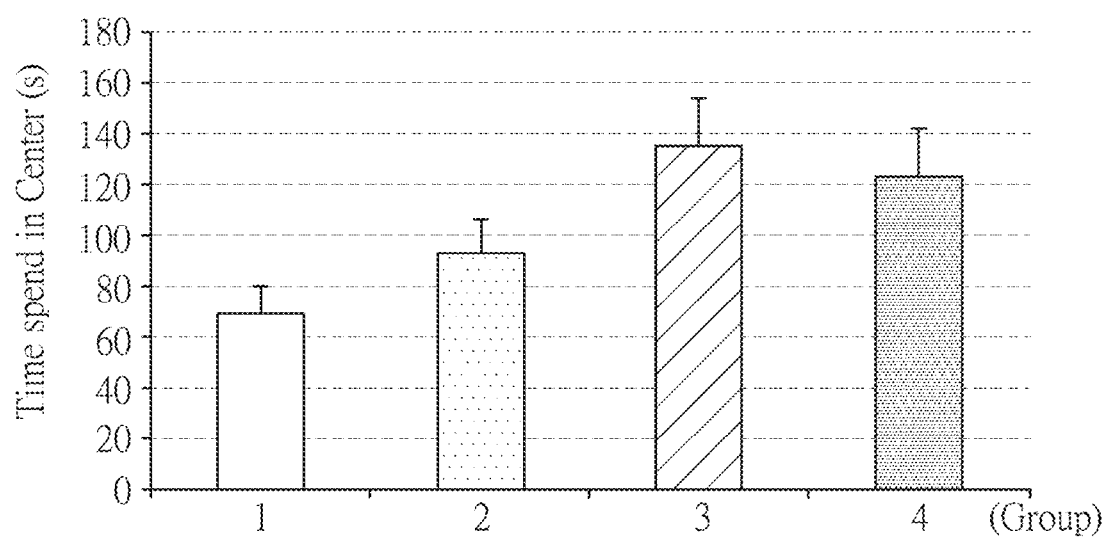
FIG. 2F is the results of statistical analysis of the time it takes for the mice in each of the groups to enter centers of the elevated plus maze, wherein the "s" of Y axis represents second.
Figure 2G:
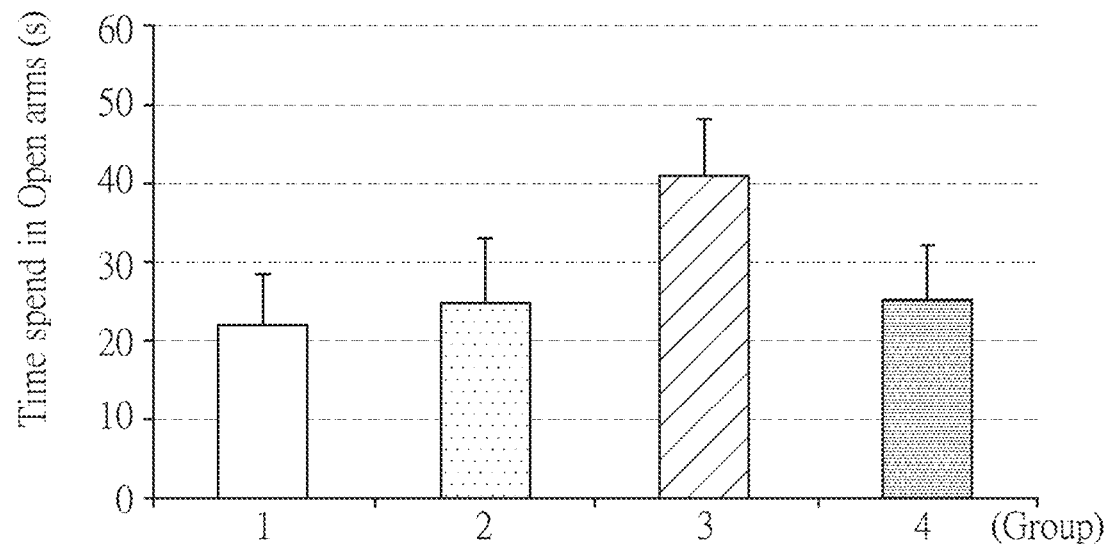
FIG. 2G is the results of statistical analysis of the time it takes for the mice in each of the groups to enter open arms of the elevated plus maze, wherein the "s" of Y axis represents second.
Figure 2H:
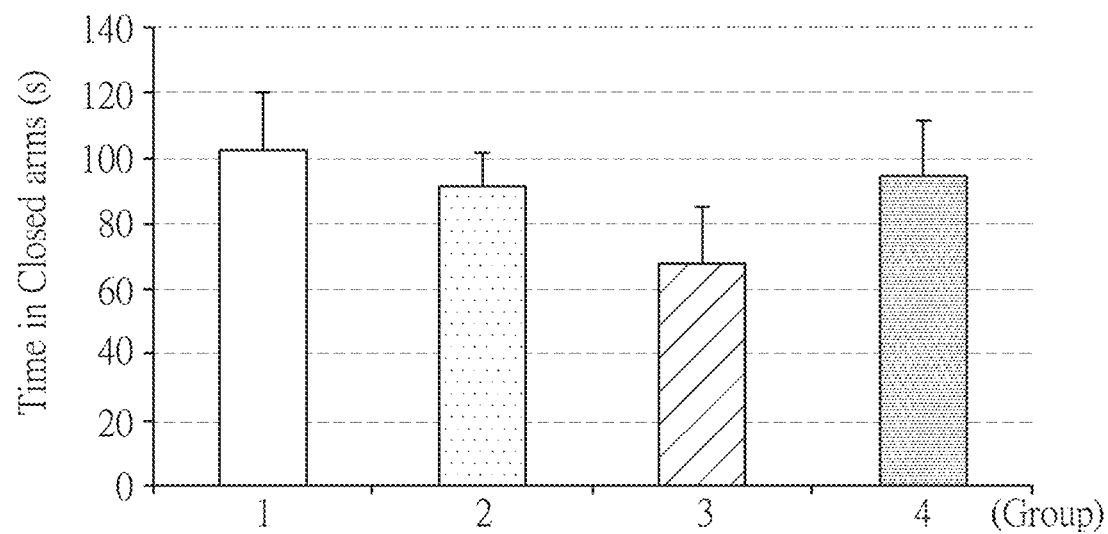
FIG. 2H is the results of statistical analysis of the time it takes for the mice in each of the groups to enter closed arms of the elevated plus maze, wherein the "s" of Y axis represents second.
Figure 3A:
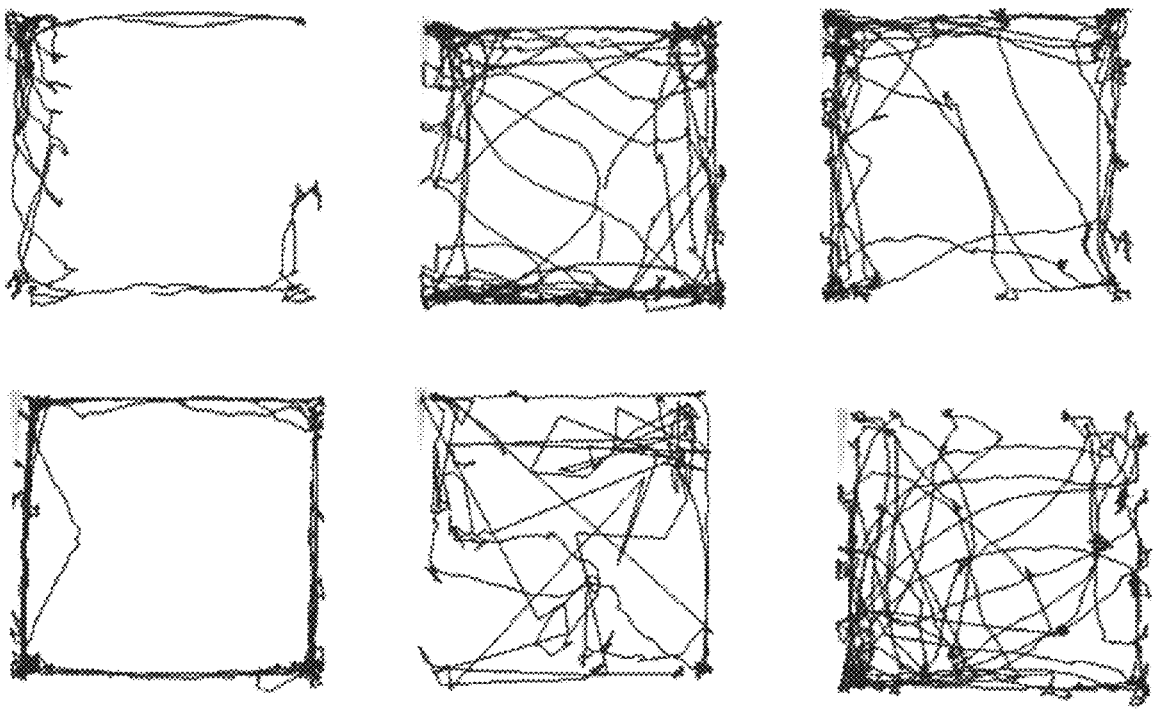
FIG. 3A shows movement paths of the first group of mice in an open field.
Figure 3B:
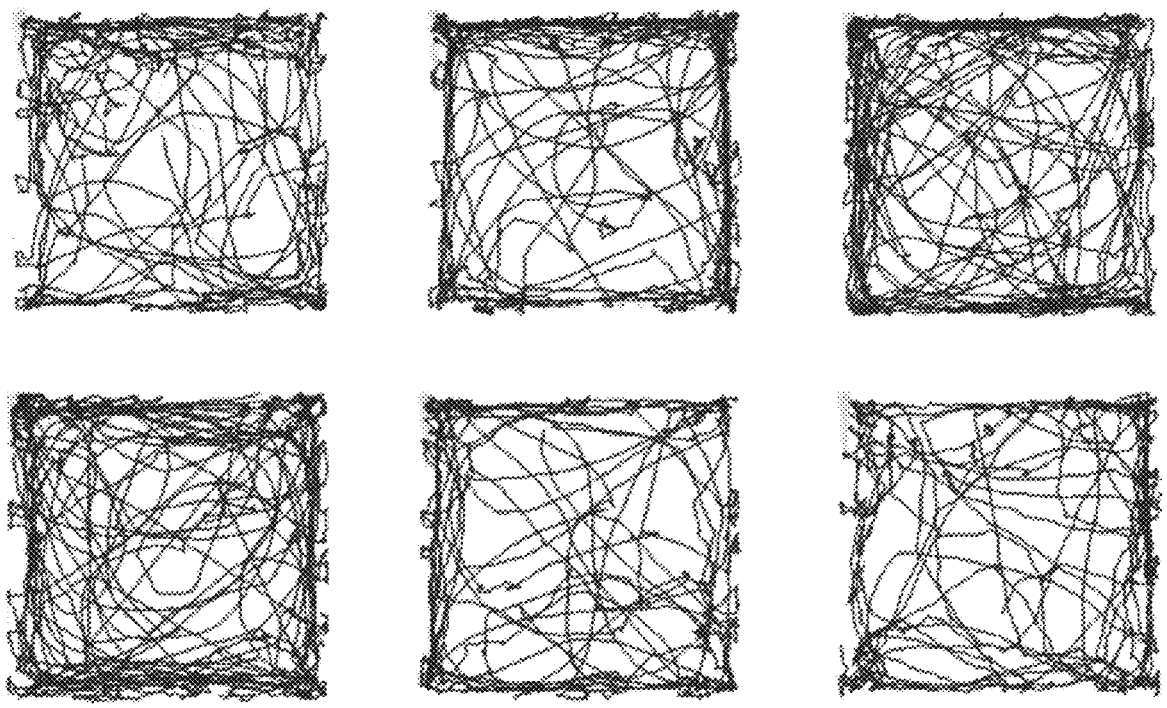
FIG. 3B shows movement paths of the second group of mice in an open field.
Figure 3C:
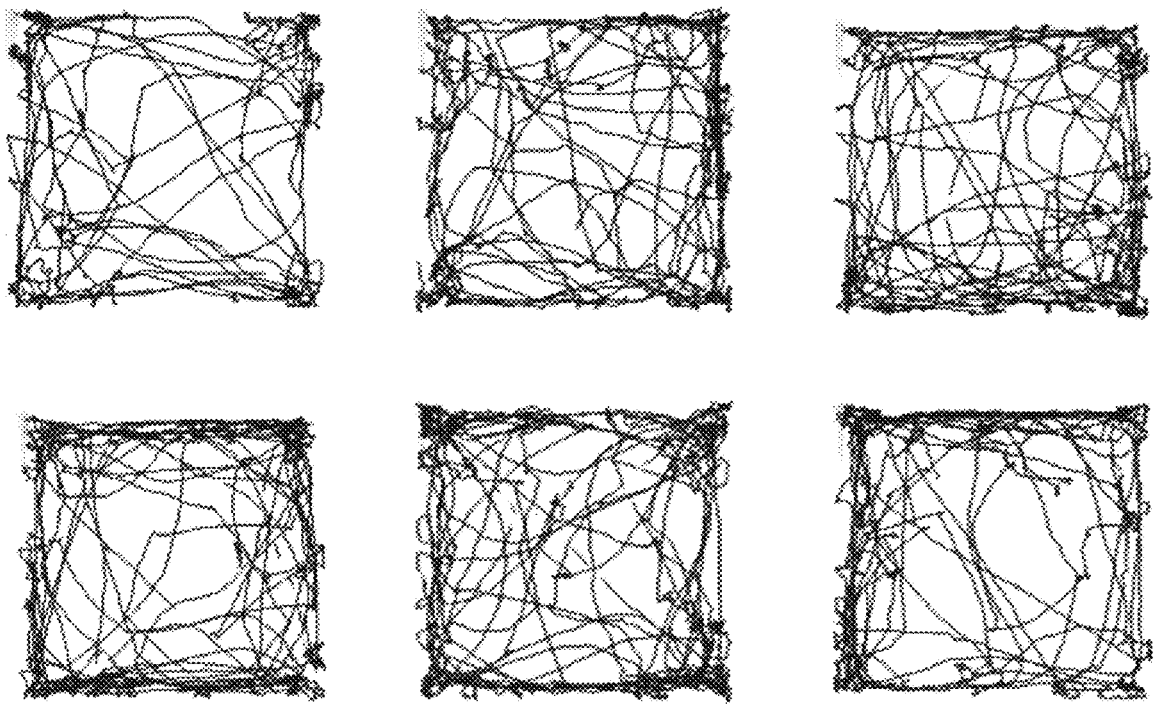
FIG. 3C shows movement paths of the third group of mice in an open field.
Figure 3D:
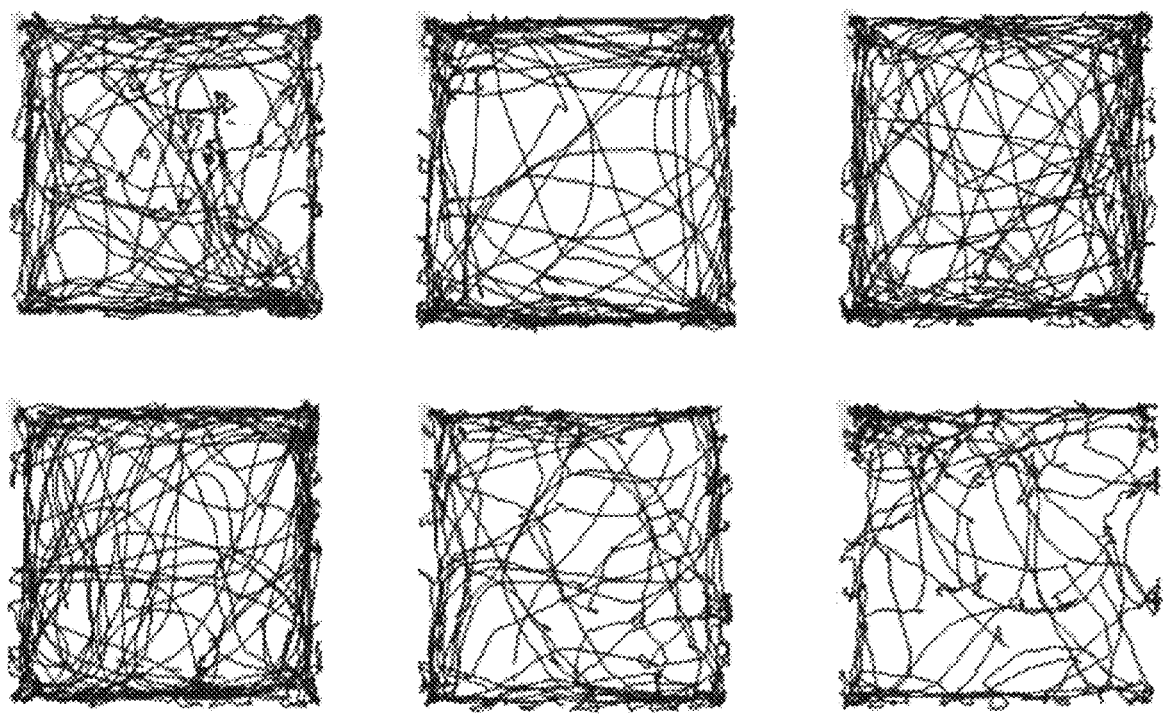
FIG. 3D shows movement paths of the fourth group of mice in an open field.
Figure 3E:
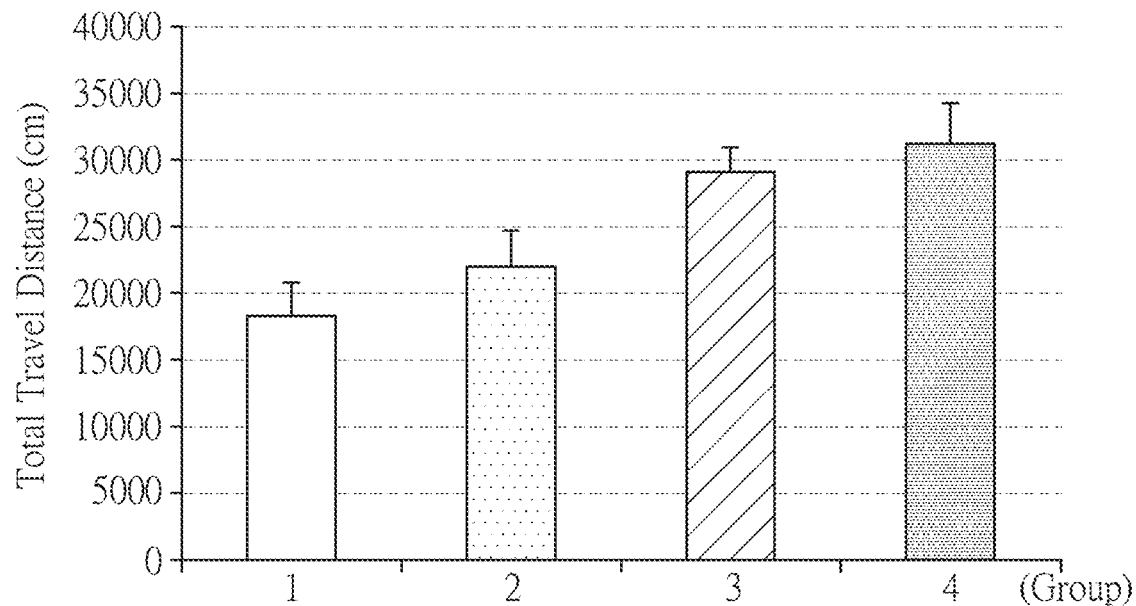
FIG. 3E is the results of statistical analysis of movement distance of the mice in each of the groups in an open field.
Figure 3F:
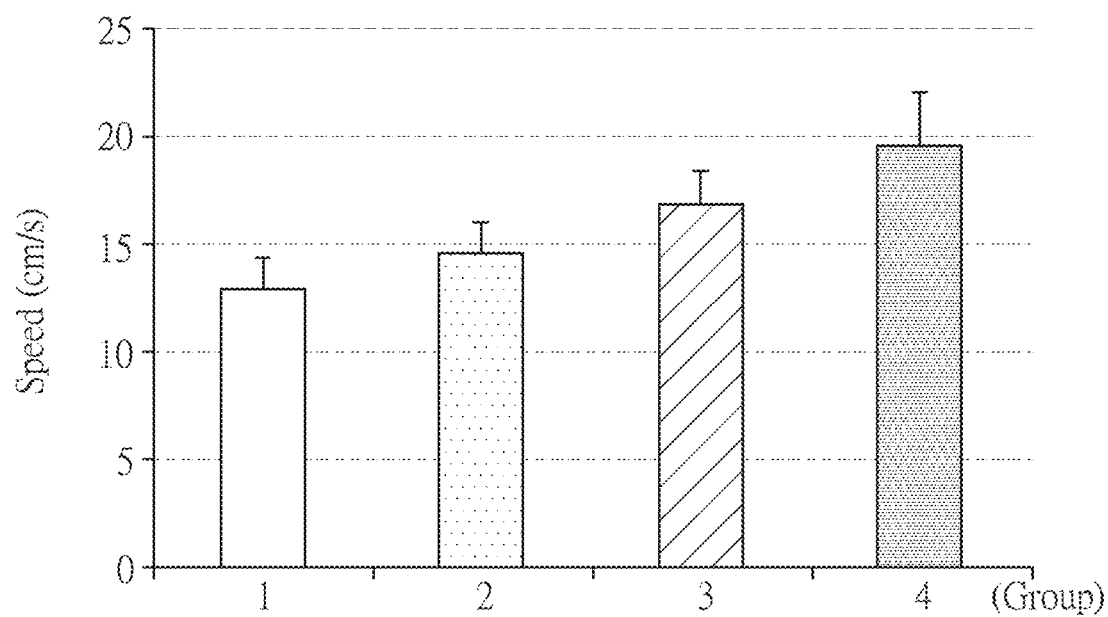
FIG. 3F is the results of statistical analysis of movement speed of the mice in each of the groups in an open field.
Figure 3G:
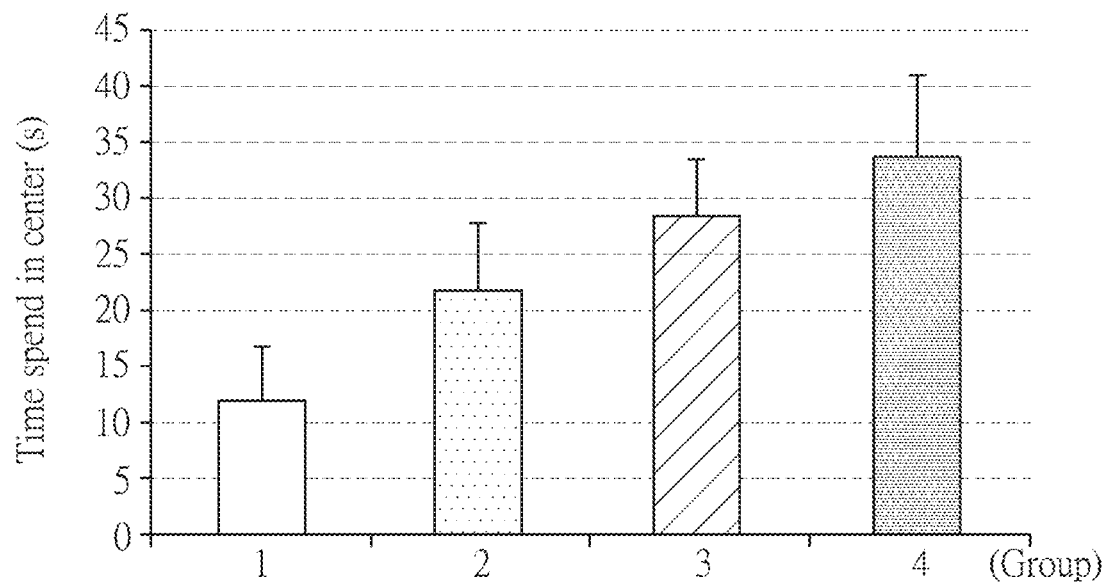
FIG. 3G is the results of statistical analysis of the time it takes for the mice in each of the groups to move to a center in an open field, wherein the "s" of Y axis represents second.
Figure 3H:
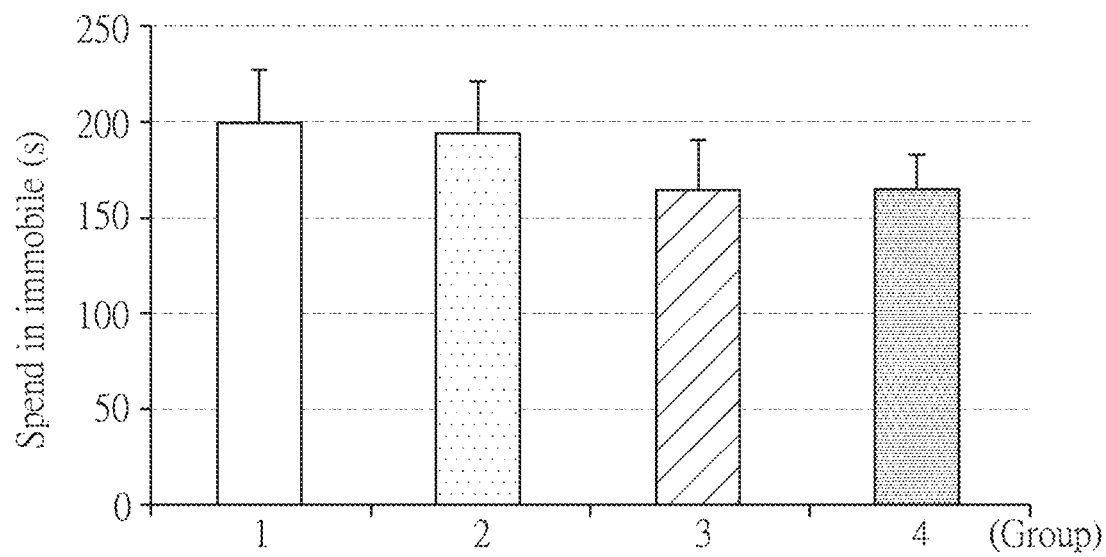
FIG. 3H is the results of statistical analysis of the time of the mice in each of the groups spent at a fixed position in an open field, wherein the "s" of Y axis represents second.

Comparing the results of FIG. 2A to FIG. 2D, it can be known that compared with the mice in the first group, the mice in the second group almost move to the open arms, the mice in the third group and the mice in the fourth group move to the open arms, and the paths of the mice in the third group in the open arms are more than that of the mice in the fourth group; also, from the results of FIG. 2F, it can be known that although the time it takes for the mice in the second to fourth groups to move to centers is longer than that of the mice in the first group, from the results of FIG. 2G and FIG. 2H, it can be known that compared with the mice in the second and fourth groups, the time of the mice in the third group on the open arms is significantly increased, and is shorter than the time on the closed arms. Therefore, the results from FIG. 2A to FIG. 2H show that by administering the composition comprising an effective amount of the kefir peptide of the invention to an individual is capable of effectively alleviating the individual's anxiety behaviors, and its effect of improving anxiety behaviors is better than that of antidepressant drugs used clinically.

Example 3: Open Field Test (OFT)

The mice in each of the groups in Example 2 are treated according to the above conditions for 30 minutes on the 8th day of rearing, and then an open field test is carried out. Specifically, the mice in each of the groups are first placed in an open field (45×45×40 cm) for 5 minutes, their travel paths and travel speeds are observed respectively, and the time it takes to reach the centers and the time spent at a fixed position are calculated. The results are shown in FIGS. 3A to 3H.

From the results of FIG. 3A to FIG. 3D, the behavior pattern of the mice in each of the groups in a new environment can be observed, and the third group of mice and the fourth group of mice are less anxious than the first group of mice; from the results of FIG. 3E to FIG. 3H, it can be known that compared with the first group of mice, the third and fourth groups of mice move a longer distance and move faster, and they are willing to spend time moving to the centers and spend less time at a certain fixed position without moving, indicating that the depressive behaviors of the third and fourth groups of mice have been improved.

From the results of this example, it can be known that the composition comprising an effective amount of the kefir peptide disclosed in the invention does have the capability to improve an individual's depressive behaviors, so the kefir peptide disclosed in the invention can be used as an active ingredient in antidepressant drugs or functional compositions.

Example 4: Forced Swimming Test (FST)

The mice in each of the groups of Example 2 are treated for 30 minutes according to the above conditions on the 7th day of rearing, and then a swimming test is carried out, testing time is 6 minutes. Movement and immobility time are measured and analyzed with a camera. The results are shown in FIG. 4, wherein the immobility time is a period of time without active movement but only floating in the water; the movement time is a period of time with active movement or circular movement.

Figure 4:
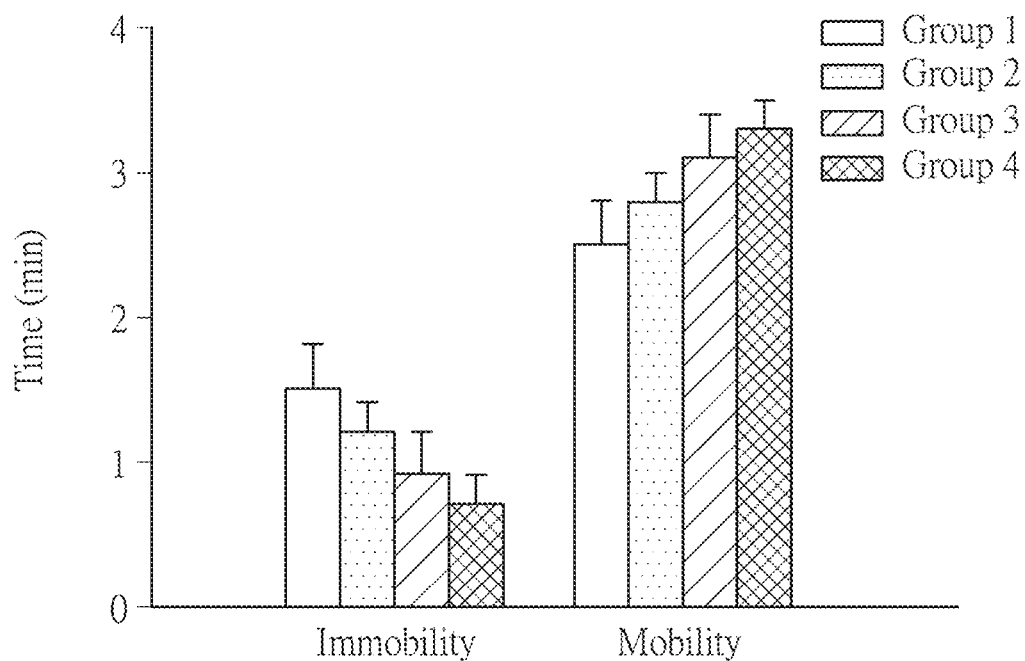
FIG. 4 is the results of statistical analysis of immobility and movement time of the mice in each of the groups in a swimming test.

From the results in FIG. 4, it can be known that the immobility and movement time of the first group of mice are 1.5±0.3 minutes and 2.5±0.3 minutes, respectively; the immobility and movement time of the third group of mice are 0.7±0.2 minutes and 3.3±0.3 minutes, respectively; the immobility and movement time of the fourth group of mice are 0.9±0.2 minutes and 3.1±0.3 minutes, respectively.

Comparison of the above results shows that compared with the first group of mice, the immobility time of the third and fourth groups of mice is significantly reduced ($P<0.05$), and the movement time is significantly increased ($P<0.05$); it can be known that by administering the composition comprising an effective amount of the kefir peptide disclosed in the invention to an individual with depressive behaviors is capable of improving the individual's depressive behaviors, and the improvement effect is close to that of antidepressant drugs used clinically.

Example 5: Tail Suspension Test (TST)

Refer to the steps of Example 2, the CD-1 mice are randomly divided into five groups and raised under the following conditions:
the first group: take distilled water orally;
the second group: take 150 mg/kg kefir fermentation product orally;
the third group: take the peptide 1 (10 mg/kg) disclosed in Example 1 orally, and the amino acid sequence is SEQ ID No: 1;
the fourth group: take the peptide 2 (10 mg/kg) disclosed in Example 1 orally, and the amino acid sequence is SEQ ID No: 2; and
the fifth group 5: take the peptide 3 (10 mg/kg) disclosed in Example 1 orally, and the amino acid sequence is SEQ ID No: 3.

When the mice in each of the groups are raised to the 7th day, after 30 minutes of treatment according to the following conditions, a tail suspension test is carried out for 6 minutes, and the immobility time is measured in the last 4 minutes. The results are shown in FIG. 5, wherein the immobility time refers to a period of time in which the mice are suspended and completely still.

Figure 5:
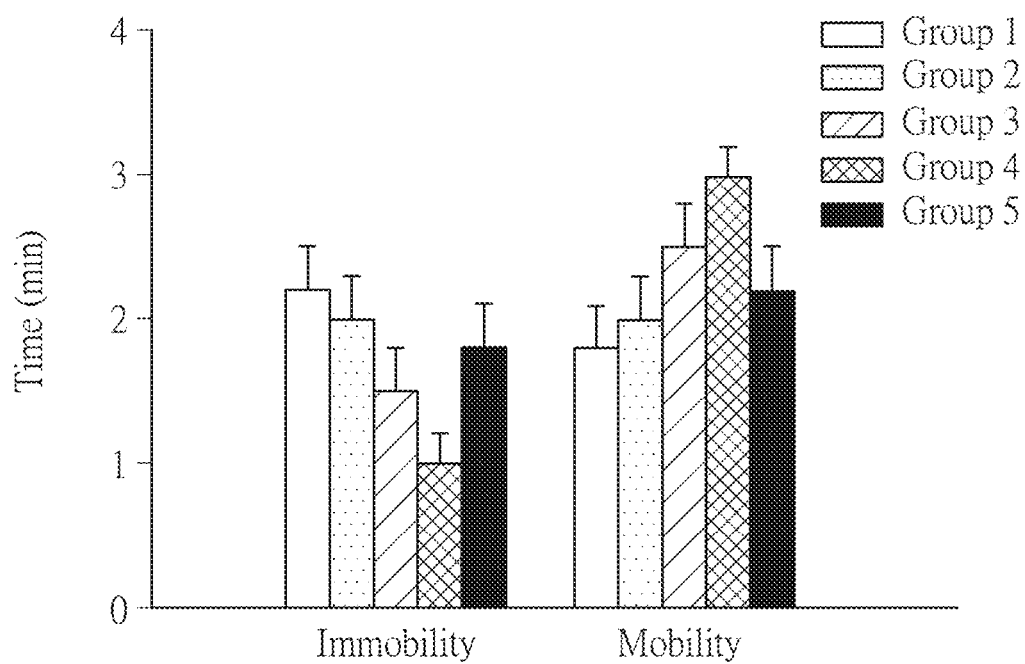
FIG. 5 is the results of statistical analysis of immobility and movement time of the mice in each of the groups in a tail suspension test.

From the results in FIG. 5, it can be known that the immobility and movement time of the first group of mice are 2.2±0.3 minutes and 1.8±0.3 minutes, respectively, while the immobility and movement time of the second, third, fourth, and fifth groups of mice are 2.0±0.3 minutes/2.0±0.3 minutes, 1.5±0.3 minutes/2.5±0.3 minutes, 1.0±0.2 minutes/3.0±0.2 minutes, and 1.8±0.3 minutes/2.2±0.3 minutes, respectively. The results in FIG. 5 show that compared with the first group of mice, the immobility time of the second group of mice administered with the kefir fermentation product is slightly reduced and the movement time is slightly increased, but comparing the data of the third group to the fifth group of mice, the immobility time ($P<0.05$) of only the fourth group of mice administered with the peptide 2 (i.e., the band 3 in FIG. 1A) is significantly reduced, and the movement time ($P<0.05$) of the mice is increased.

From the results of Examples 2 to 4, it can be clearly known that by administering the kefir fermentation product is capable of effectively improving the depressive behaviors and related diseases of a depressive individual, and the results of this example further confirm that the peptide 2 in the kefir fermentation product has an antidepressant activity, which means that by administering an effective amount of the peptide 2 (that is, the kefir peptide disclosed in the invention) is capable of achieving an efficacy of treating or preventing depressive behaviors and diseases related to depressive behaviors.

Example 6: Protein Expression Analysis

Expressions of protein and mRNA in the hippocampal tissues of the mice in each of the groups in Example 2 are assessed by quantitative RT-PCR method and western blot analysis, and the results are shown in FIG. 6 and FIG. 7, respectively.

Figures 6A, 6D:
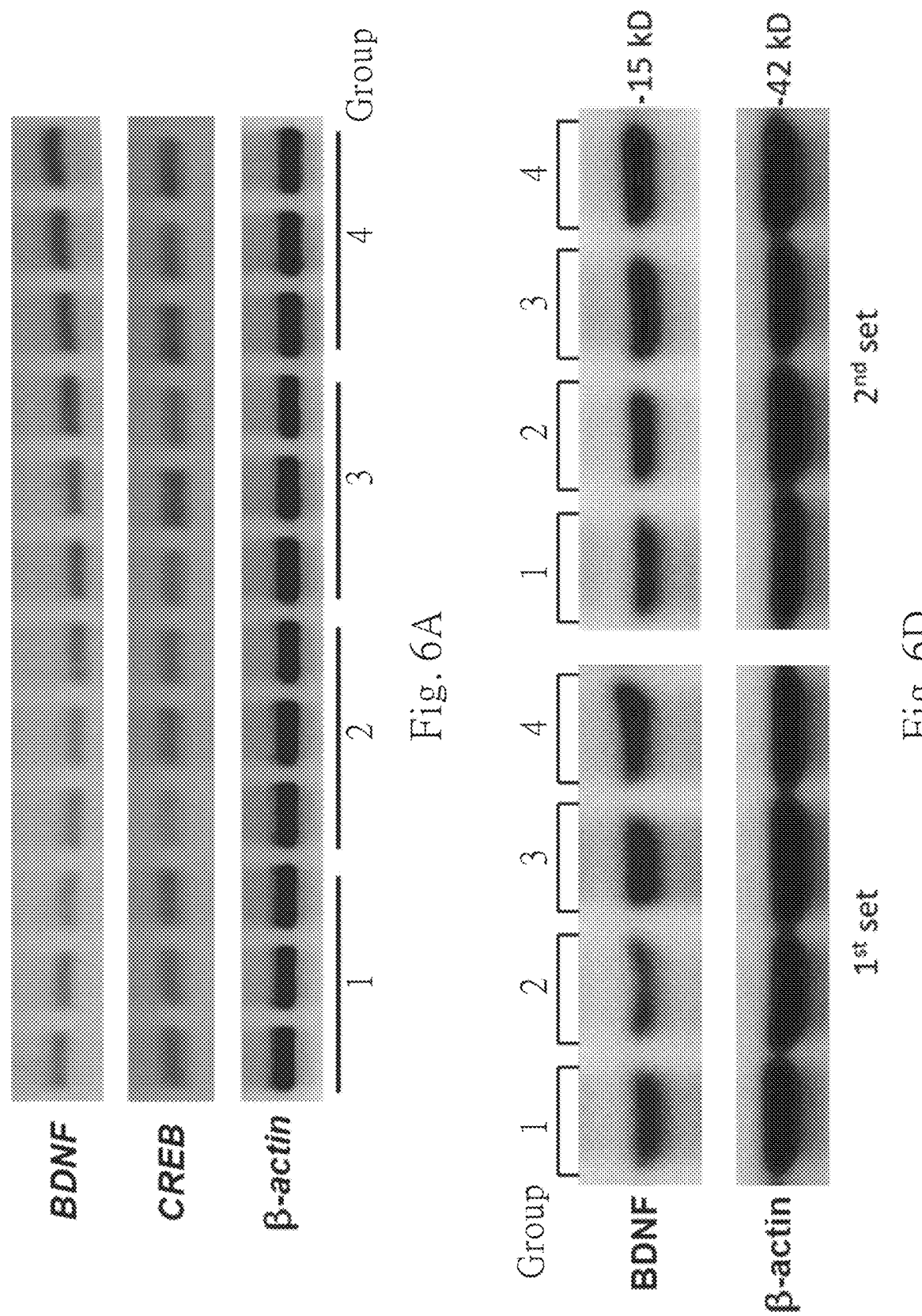
FIG. 6A is the expression results of BDNF (brain-derived neurotrophic factor) and CREB (cAMP responsive element-binding protein) mRNA in hippocampal tissues of the mice in each of the groups analyzed by quantitative RT-PCR.
FIG. 6D is the results of BDNF and CREB protein expressions in the hippocampal tissues of the mice in each of the groups assessed by western blot analysis.
Figure 6B:
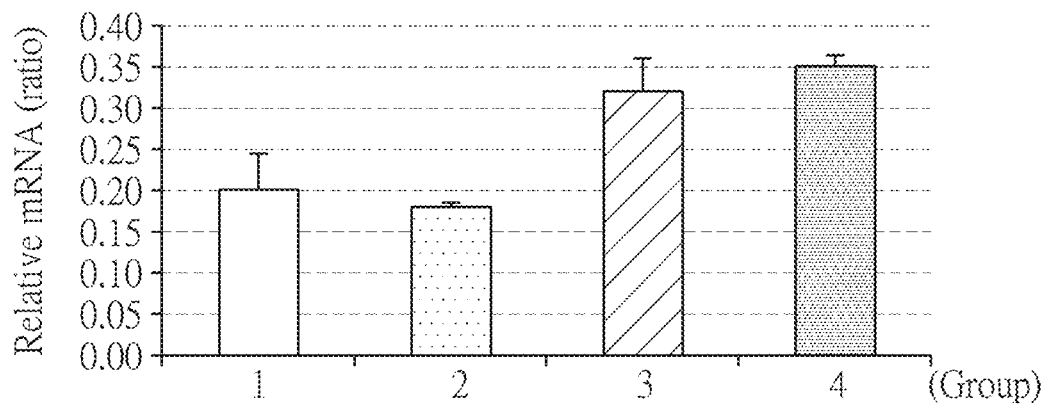
FIG. 6B is the results of quantifying the BDNF mRNA expression levels in the hippocampal tissues of the mice in each of the groups.
Figure 6C:
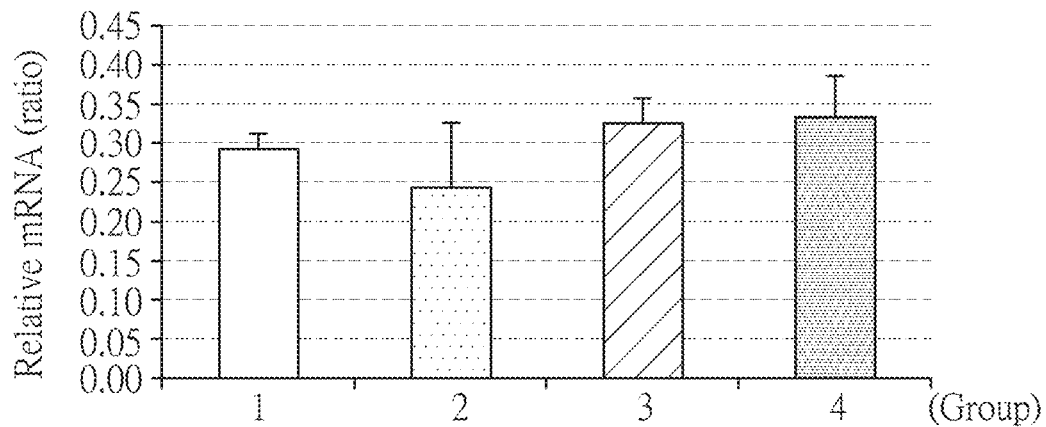
FIG. 6C is the results of quantifying the CREB mRNA expression levels in the hippocampal tissues of the mice in each of the groups.
Figure 6E:
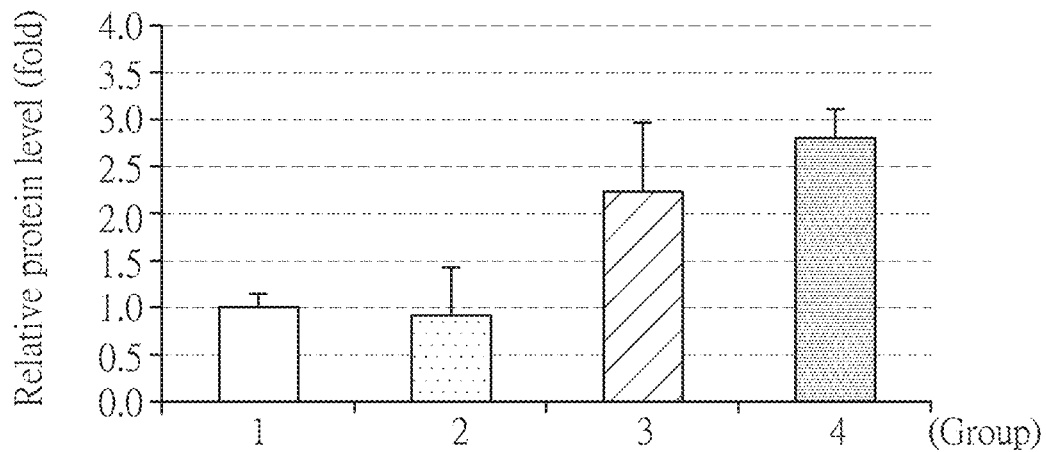
FIG. 6E is the results of quantifying BDNF protein expression levels in the hippocampal tissues of the mice in each of the groups.

From the results in FIG. 6A to FIG. 6C, it can be known that CREB (cAMP responsive element-binding protein) mRNA in the hippocampal tissues of the mice in each of the groups has not changed significantly, and compared with the first group of mice, expressions of BDNF mRNA in the third and fourth groups of mice can be significantly improved; further, from the results in FIG. 6D, it can be known that compared with the first group of mice, expression levels of BDNF protein in the hippocampal tissues of the third and fourth groups of mice are both increased by more than 2 times.

Figure 7A:
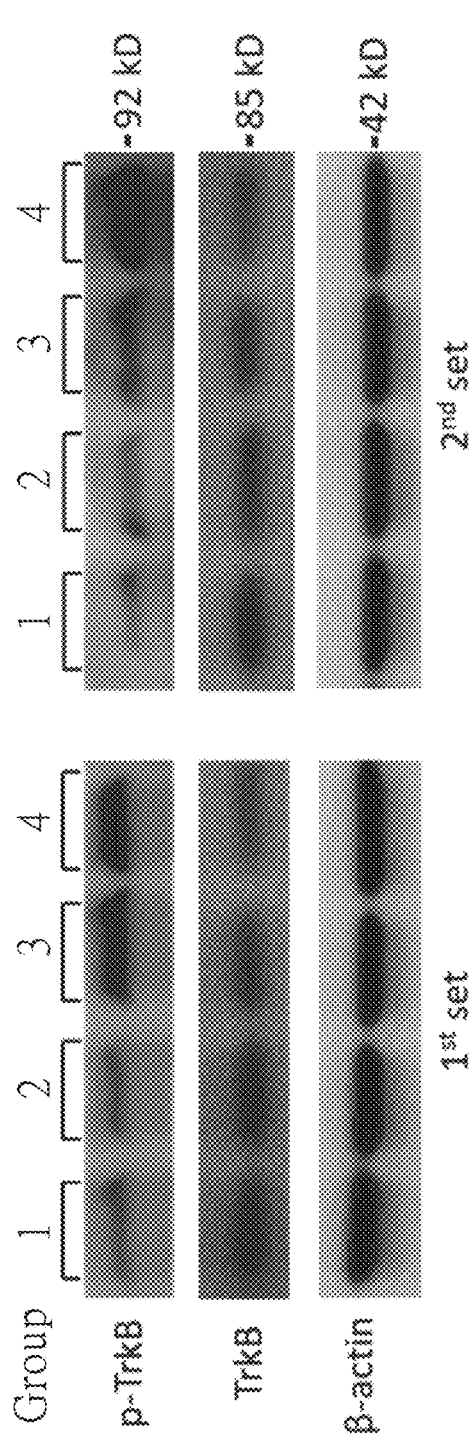
FIG. 7A is the results of protein expression levels of p-TrkB (phosphorylated-TrkB)/TrkB protein in the hippocampal tissues of the mice in each of the groups assessed by western blot analysis.
Figure 7D:
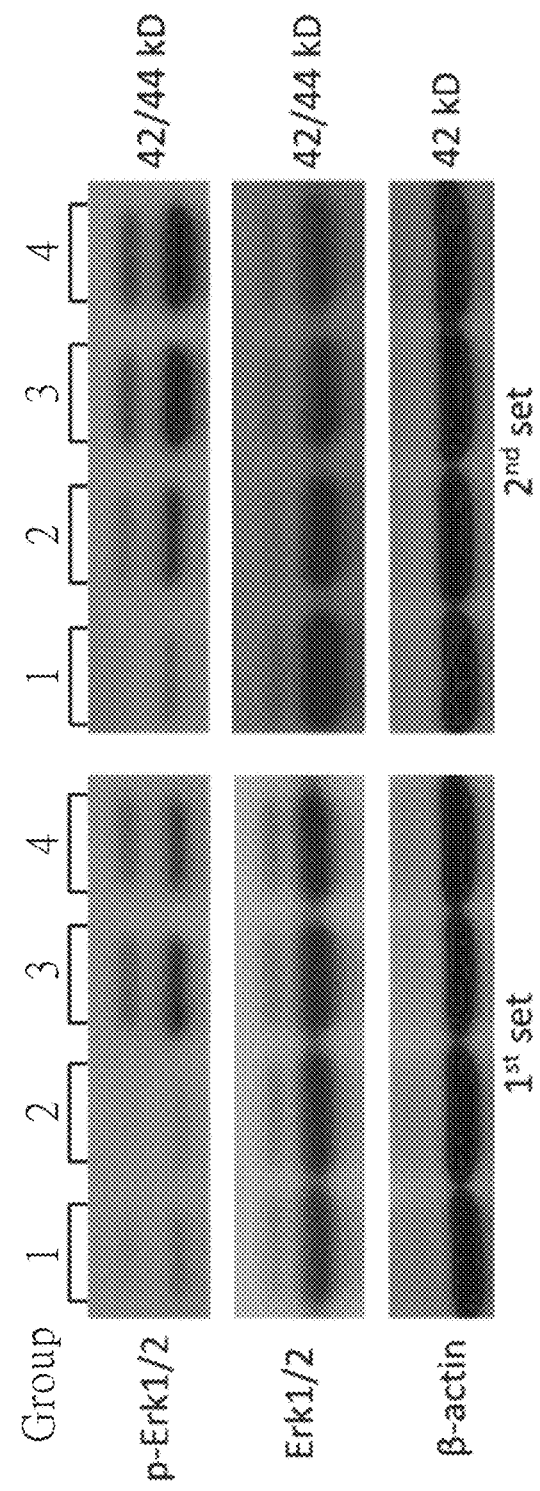
FIG. 7D is the results of protein expression levels of p-Erk1/2 (phosphorylated-ERK1/2)/Erk1/2 protein in the hippocampal tissues of the mice in each of the groups assessed by western blot analysis.
Figure 7B:
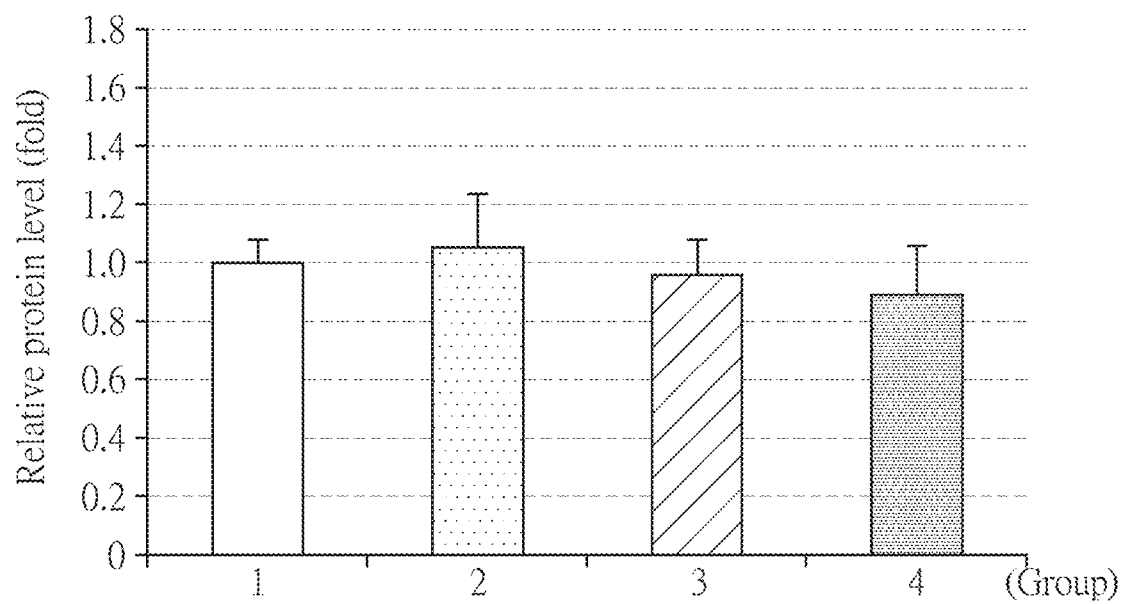
FIG. 7B is the results of quantifying the expression levels of total TrkB protein in the hippocampal tissues of the mice in each of the groups.
Figure 7C:
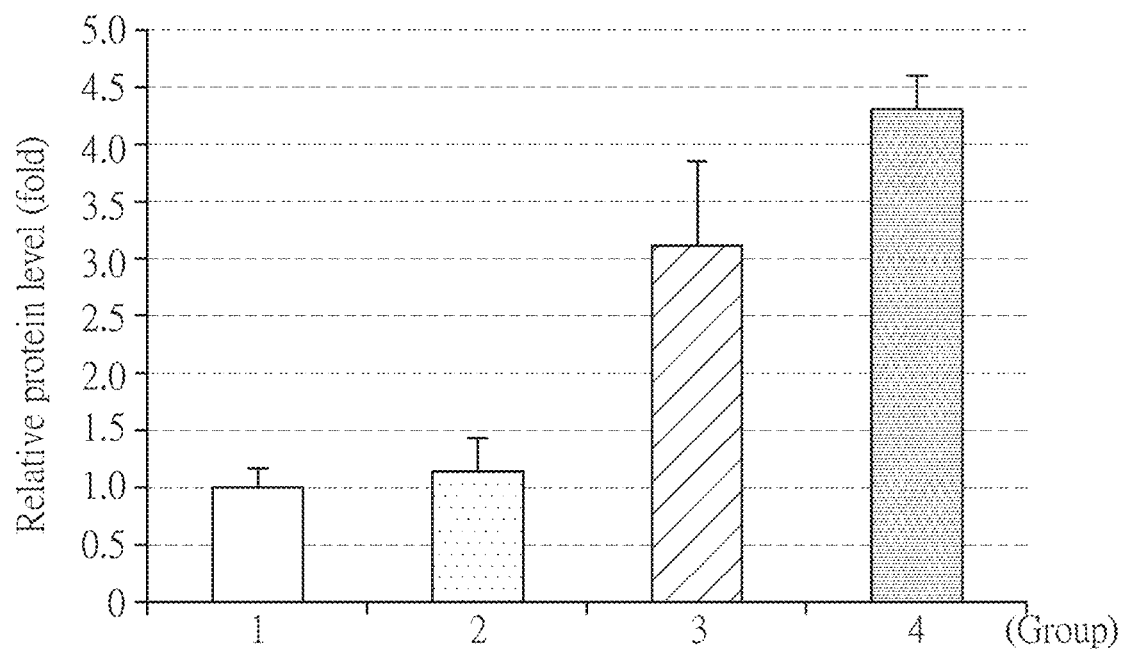
FIG. 7C is the results of quantifying the expression levels of p-TrkB protein relative to total TrkB protein in the hippocampal tissues of the mice in each of the groups.
Figure 7E:
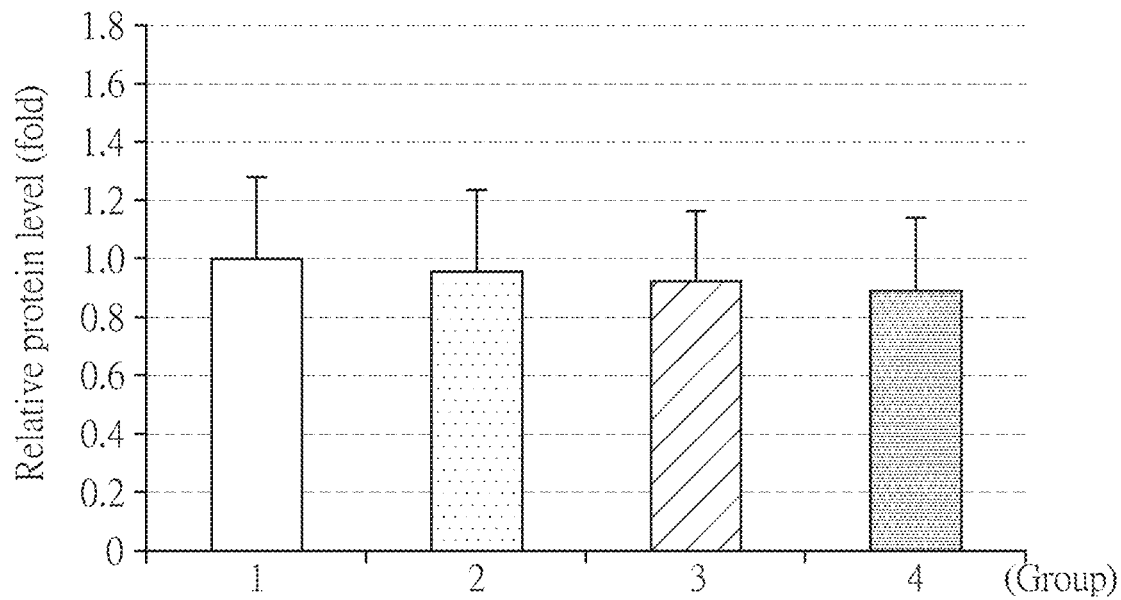
FIG. 7E is the results of quantifying the expression levels of total Erk1/2 protein in the hippocampal tissues of the mice in each of the groups.
Figure 7F:
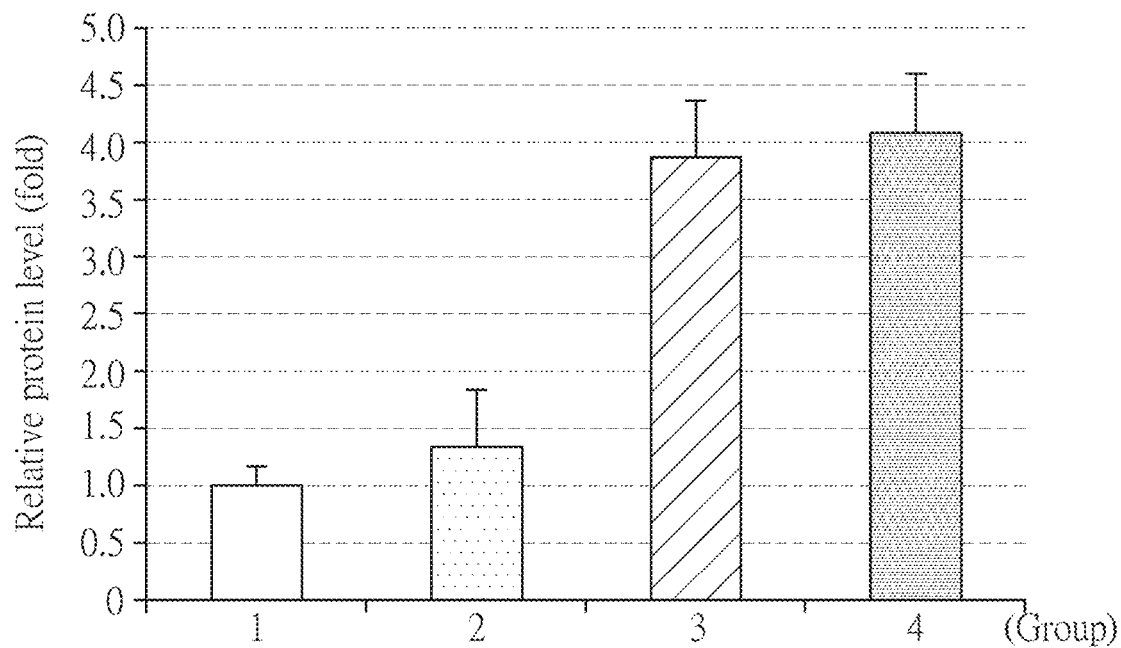
FIG. 7F is the results of quantifying the expression levels of p-Erk1/2 protein relative to total Erk1/2 protein in the hippocampal tissues of the mice in each of the groups.

Furthermore, it can be known from the results of FIG. 7B and FIG. 7D that compared with the first group of mice, expression levels of TrkB and Erk1/2 protein in the hippocampal tissues of the third and fourth groups of mice have not change significantly, but it can be known from the results of FIG. 7C and FIG. 7E that a phosphorylation status of p-Erk1/2/Erk1/2 and p-TrkB/TrkB in the hippocampal tissues of the third and fourth groups of mice increases significantly ($P<0.05$).

The results of FIGS. 6 and 7 show that by administering the composition comprising the kefir peptide disclosed in the invention, such as the kefir fermentation product, is capable of effectively enhancing an expression level of BDNF protein in the hippocampal tissues of an individual, and enhancing an expression level of phosphorylation of p-Erk1/2/Erk1/2, and p-TrkB/TrkB, thus confirming that the kefir peptide disclosed in the invention or the composition comprising the kefir peptide disclosed in the invention is capable of effectively preventing or improving depressive behaviors and diseases related to depressive behaviors.

It is to be understood that the above description is only the embodiments and examples of the invention and is not used to limit the present invention, and changes in accordance with the concepts of the present invention may be made without departing from the spirit of the present invention. For example, the equivalent effects produced by various transformations, variations, modifications and applications made to the configurations or arrangements shall still fall within the scope covered by the appended claims of the present invention.

What is claimed is:

1. A method for treating depression, comprising administering an effective amount of a composition to a subject in need thereof for enhancing an expression of brain-derived neurotrophic factor (BDNF) in hippocampal tissues of the subject and activating a BDNF/TrkB information channel, thereby improving or alleviating the depressive behaviors or symptoms of depression of the subject;
   wherein the composition comprises a purified kefir peptide, and an amino acid sequence of the kefir peptide comprises a sequence of SEQ ID No: 2.

2. The method of claim 1, wherein the amino acid sequence of the purified kefir peptide is SEQ ID No: 2.

3. The method of claim 1, wherein the composition further comprises a purified peptide with an amino acid sequence of SEQ ID No: 1.

4. The method of claim 1, wherein the composition further comprises another purified peptide with an amino acid sequence of SEQ ID No: 3.

5. The method of claim 2, wherein the composition further comprises another purified peptide with an amino acid sequence of SEQ ID No: 3.

6. The method of claim 3, wherein the composition further comprises another purified peptide with an amino acid sequence of SEQ ID No: 3.

* * * * *

SEQUENCE LISTING

```
<160> NUMBER OF SEQ ID NOS: 3

<210> SEQ ID NO 1
<211> LENGTH: 17
<212> TYPE: PRT
<213> ORGANISM: Artificial Sequence
<220> FEATURE:
<223> OTHER INFORMATION: artificiall obtained

<400> SEQUENCE: 1

Thr Glu Ile Pro Ala Ile Asn Thr Ile Ala Ser Ala Glu Pro Thr Val
1               5                   10                  15

His

<210> SEQ ID NO 2
<211> LENGTH: 15
<212> TYPE: PRT
<213> ORGANISM: Artificial Sequence
<220> FEATURE:
<223> OTHER INFORMATION: artificiall obtained

<400> SEQUENCE: 2

Tyr Gln Glu Pro Val Leu Gly Pro Val Arg Gly Pro Phe Pro Ile
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: artificiall obtained

<400> SEQUENCE: 3

Lys Leu His Leu Pro Leu Pro Leu Val Gln Ser Trp Met
1               5                   10
```